United States Patent [19]

Benoit et al.

[11] Patent Number: 5,792,902
[45] Date of Patent: Aug. 11, 1998

[54] DYSLIPOPROTEINAEMIA-SENSITIZED TRANSGENIC RABBIT

[75] Inventors: Patrick Benoit, Paris; Patrice Denefle, Saint Maur; Nicolas Duverger, Paris; Louis Marie Houdebine, Buc, all of France

[73] Assignee: Rhone-Poulenc Rorer S.A., Antony Cedex, France

[21] Appl. No.: 704,582

[22] PCT Filed: Mar. 16, 1995

[86] PCT No.: PCT/FR95/00318

§ 371 Date: Sep. 20, 1996

§ 102(e) Date: Sep. 20, 1996

[87] PCT Pub. No.: WO95/25793

PCT Pub. Date: Sep. 28, 1995

[30] Foreign Application Priority Data

Mar. 21, 1994 [FR] France ................. 94 03263

[51] Int. Cl.$^6$ ........................... C12N 15/00; A61K 49/00
[52] U.S. Cl. ........................... 800/2; 435/172.3; 424/9.1; 424/9.2
[58] Field of Search ................. 800/2, DIG. 1, 800/DIG. 2, DIG. 3, DIG. 4; 435/172.3

[56] References Cited

FOREIGN PATENT DOCUMENTS

WO 93/19166   9/1993   WIPO.

OTHER PUBLICATIONS

Perevozchikov et al., Human APO A-1 cDNA Gene Expression in Transgenic Rabbits: Modeling of the Neurological Syndrome of Human Tangier Disease, Biological Abstracts, 96.3, Abst. No. 28308, (1993).

Chowdhury et al., Long-Term Improvement of Hypercholesterolemia After ex Vivo Gene Therapy in LDLR-Deficient Rabbits, Science, 254, 1802–1804, (1991).

Schultz et al., Protein Composition Determines the Anti-Atherogenic Properties of HDL in Transgenic Mice, Nature, 365, 6448, 762–764, (1993).

Latta et al., Human Alpolipoprotein AII Can Be Overproduced as A Recombinant Protein From E-coli, Circulation, 86, 4, 133, (1992).

Duverger et al., Functional Characterization of Human Recombinant Apolipoprotein AIV Produced in Escherichia coli, Euro. Journal of Biochemistry, 201, 2, 373–383, (1991).

Perevozchikov et al. Expression of Human Apolipoprotein A–1 gene cDNA in Transgenic Rabbits: Modeling of the Neurologic Syndrome of Human Tangier Disease, Molecular Biology, vol. 27, No. 1, pp. 6–14, Jan. 2, 1993.

Hoeg et al, Development of transgenic watanabe heritable hyperlipidemic rabbits expressing human apoA–1. Circulation, vol. 88, No. 4, part 2, #0010, Oct. 1993.

*Primary Examiner*—Jasemine C. Chambers
*Assistant Examiner*—Deborah J. R. Clark

[57] ABSTRACT

A transgenic rabbit expressing a protein capable of interfering with dyslipoproteinaemia-related diseases, a method of preparing the same, and its use as an animal model, are disclosed. Specifically, a transgenic rabbit expressing high levels of Apo-AI, is disclosed.

20 Claims, 6 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:1:

TGGCTTTCTC GCCAAGTGTC TTCAGGTGG    29

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:2:

GACAGCGGCA GAGACTATGT GTCCCAGTTT GAA    33

DYSLIPOPROTEINAEMIA-SENSITIZED TRANSGENIC RABBIT

This application is a 35 U.S.C. § 371 national application of PCT International Patent Application No. PCT/FR95/00318, filed Mar. 16, 1995, and claims priority pursuant to 35 U.S.C. § 119 of French patent application No. 94/103263, filed Mar. 21, 1994.

The present invention relates to a transgenic rabbit which expresses a protein which is capable of interfering in diseases which are linked to dyslipoproteinaemias, to the process for its preparation and to its use as an animal model.

Dyslipoproteinaemias are disorders in the metabolism of the lipoproteins which are responsible for transporting lipids such as cholesterol and triglycerides in the blood and the peripheral fluids. They lead to important diseases, such as, in particular, atherosclerosis, which diseases are linked, respectively, to hypercholesterolaemia, hypocholesterolaemia or hypertriglyceridaemia.

Atherosclerosis is a complex, polygenic disease which is defined, on the histological plane, by deposits (lipid or fibro-lipid plaques) of lipids and other blood derivatives in the wall of the large arteries (aorta, coronary arteries and carotid). These plaques, which are more or less calcified according to the progress of the disease, can be associated with lesions and are linked to the accumulation, in the arteries, of fatty deposits which essentially consist of cholesterol esters. These plaques are accompanied by a thickening of the arterial wall together with hypertrophy of the smooth muscle, the appearance of foam cells and the accumulation of fibrous tissue. The atheromatous plaque is very clearly raised on the wall, thereby conferring on it a stenosing character which is responsible for the vascular occlusions, by means of atheroma, thrombosis or embolism, which occur in the worst-affected patients. Hypercholesterolaemias can, therefore, lead to very serious cardiovascular diseases such as infarction, sudden death, cardiac decompensation, cerebrovascular diseases, etc.

It is particularly important, therefore, to have immediately available treatments which diminish, in some disease situations, the levels of plasma cholesterol or stimulate the efflux of cholesterol (reverse transport of cholesterol) from the peripheral tissues in order to unload the cells which have accumulated the cholesterol in the context of forming an atheroma plaque. (Cholesterol is transported in the blood by a variety of lipoproteins including the low density lipoproteins (LDL) and the high density lipoproteins (HDL). The LDLs are synthesized in the liver and are responsible for supplying the peripheral tissues with cholesterol. By contrast, the HDLs pick up cholesterol in the peripheral tissues and transport it to the liver where it is stored and/or broken down).

From this point of view, it would be worthwhile to have available an animal model which was capable of expressing a protein which was able to interfere in the diseases which are linked to dyslipoproteinaemias. Such an animal model would be particularly advantageous for understanding these diseases and, more specifically, the regulatory mechanisms which they initiate. It would make it possible to test, rapidly and in vivo, a considerable number of therapeutic agents for the purpose of detecting a potential activity associated with the expression of the said proteins. Furthermore, such a model would be of interest for developing novel therapeutic methods for treating this type of disease, such as methods which are based on gene therapy, for example.

The specific object of the present invention is to propose a rabbit which has been genetically modified in this sense.

Generally speaking, the murines, namely mice, rats and guinea pigs, are the most widely used animal models. They are easy to manipulate and inexpensive. Unfortunately, these small mammals are not always compatible with the intended application. Thus, they are not always representative of the human model and its metabolism. Closer to man, the chimpanzee is a test animal which is used, in particular, for detecting therapeutic agents and vaccines which are directed against AIDS and cancer. However, its very substantial cost constitutes a major and compelling handicap with regard to its use.

Within the scope of the present invention, the rabbit has proved to be the appropriate animal model. A comprehensive knowledge exists of the metabolism of the rabbit and of the diseases of this animal which are linked to lipoproteins. The rabbit is an animal which is classified as "LDL mammalian", that is to say the LDLs are the major transporters of plasma cholesterol as in man, contrary to rats and mice, which are animals classified as "HDL mammalian". Furthermore, a large number of genetic variations exist in the lipoproteins within the rabbit lines, such as the WHHL rabbits which are deficient in LDL receptor (Watanabe heritable hyperlipidaemic rabbit) or else the "St Thomas Hospital" rabbits, which overproduce LDLs (Rosenfeld et al., 1990, Arteriosclerosis 10, 680–687; Sedon et al.; 1987, Arteriosclerosis 7, 113–124).

More specifically, the present invention relates to a transgenic rabbit into whose genome has been inserted at least one exogenous genomic DNA sequence which encodes a protein which is capable of interfering in diseases linked to dyslipoproteinaemias.

A transgenic rabbit according to the invention can integrate the genomic DNA sequence into all its cells or only into a certain percentage of cells; in the latter case it would be termed mosaic. In general, the genomic DNA sequence is integrated into all the cells.

Within the meaning of the present invention, the designation "protein which is capable of interfering in diseases linked to dyslipoproteinaemias" is understood to cover the apolipoproteins and any proteinaceous product which has an activity which is linked to the cardiovascular diseases. Preferably, the term proteinaceous product denotes any mutant, fragment or peptide which possesses at least one biological property of an apolipoprotein, as well as any natural variant of the apolipoproteins.

In accordance with the invention, a genomic DNA sequence is understood to mean genomic DNA or a hybrid construct which consists, for example, of a cDNA into which one or more introns have been inserted.

Preferably, the genomic DNA sequence is a human genomic DNA sequence.

Advantageously, the use of genomic DNA rather than complementary DNA leads to expression levels which are markedly higher.

The inserted genomic DNA sequence according to the invention encodes all, or an active part, of at least one protein which is involved in lipoprotein metabolism. The protein can be:

- an apolipoprotein which is selected, for example, from among the apolipoproteins A-I, A-II, A-IV, B, C-I, C-II, C-III, D, E, F, G, H, J and apo(a),
- an enzyme such as lipoprotein lipase, hepatic lipase or lecithin cholesterol acyltransferase,
- a lipid transfer protein such as the cholesterol ester transfer protein and the phospholipid transfer protein,
- an HDL binding protein, or else
- a receptor which is selected, for example, from among the LDL receptors, the chylomicron remnant receptors and the scavenger receptors.

Naturally, this list which is presented does not limit the scope of the invention. This genomic DNA sequence can also contain several genes which are organized, if need be, in cluster form.

Those inserted DNA sequences within the meaning of the present invention which may more specifically be cited are the genes which encode all or an active part of apolipoproteins AI, B, AIV or E, or a variant or a derivative of these apolipoproteins.

Apolipoprotein AI is a protein which consists of 243 amino acids and which is synthesized in the form of a preproprotein of 267 residues, having a molecular mass of 28,000 daltons. In man, it is synthesized specifically in the liver and the intestine and it constitutes the essential protein of the HDL particles (70% of their weight in proteins). It is abundant in the plasma (1.0–1.2 g/l). While its activity which is best characterized from the biochemical point of view is activation of lecithin-cholesterol acyltransferase (LCAT), a large number of other activities are attributed to it, such as, in particular, stimulation of the efflux of cellular cholesterol. The physiological role of apolipoprotein AI appears to be counterbalanced by apolipoprotein AII since, in man, the ratio of the two plasma concentrations (AII/AI) is very closely correlated with coronary risk. Apolipoprotein AI plays a major role in resistance to atherosclerosis, which role is probably linked to the reverse transport of cholesterol, since expression of this apolipoprotein alone in transgenic mice results in the surface of the lipid deposits in the aorta being reduced 40-fold as compared with control mice (Rubin et al. 1993 Science, vol 365 p 762). Its gene, which is 1863 bp in length, has been cloned and sequenced (Sharpe et al., Nucleic Acids Res. 12(9) (1984) 3917). Those proteinaceous products having an activity of the apolipoprotein AI type which may in particular be mentioned are the natural variants described in the prior art (the following table).

| Variant: | Mutation | Variant | Mutation |
|---|---|---|---|
| Milano | Arg173Cys | Norway | Glu136Lys |
| Marburg | Lys107φ | | Pro165Arg |
| Munster2B | Ala158Glu | | Pro3His |
| Giessen | Pro143Arg | | Arg10Leu |
| Munster3A | Asp103Asn | | Gly26Arg |
| Munster3B | Pro4Arg | | Asp89Glu |
| Munster3C | Pro3Arg | | Lys107Met |
| Munster3D | Asp213Gly | | Glu139Gly |
| Munster4 | Glu198Lys | | Glu147Val |
| Yame | Asp13Tyr | | Ala158Glu |
| | Asp213Gly | | Glu169Gln |
| | | | Arg177His |

Apolipoprotein B-100 is the major protein constituent of very low density lipoproteins (VLDL), low density lipoproteins (LDL) and lipoprotein Lp(a). This protein is the physiological ligand of the LDL receptor, and its plasma concentration is positively correlated with the development of atherosclerosis (Brunzell et al. 1984 Arteriosclerosis 4, 79–93). ApoB-100 is one of the largest known proteins, with a mass of 550 kDa and containing 4536 amino acids (Chen et al. 1986 J. biol. Chem, 261, 12919–21). This apolipoprotein is only synthesized in the liver. Its plasma concentration is 1.0–1.2 g/l. ApoB-100 plays the major role in transporting cholesterol which is synthesized in the liver through the plasma to the other cells of the organism. Another version of apoB, i.e. apoB-48, is present in the chylomicrons. In man, apoB-48 is synthesized in the intestine. ApoB-48 has a mass of 260 kDa and contains 2152 amino acids which linearly correspond to 48% of the N-terminal end of apoB-100 (Powell et al., 1987, Cell 50, 831–40). Since the C-terminal moiety of apoB-100 contains the zone for binding the apoB-100 to the LDL receptor, apoB-48 does not attach to this latter receptor and behaves in a different manner metabolically.

Apolipoprotein AIV (apoAIV) is a protein which consists of 376 amino acids and which is specifically synthesized in the intestine in the form of a precursor having 396 residues. The plasma protein is relatively abundant (0.16 g/l) and has a molecular mass of 46,000 daltons. While it is a major component of the chylomicrons which are secreted into the lymph, it exhibits the peculiarity of being preponderantly in a form which is not associated with lipoproteins in the plasma (R. B. Weinberg et al., 1983, J. Lipid. Research, 24: 52–59). Furthermore, plasma apoAIV is polymorphic, although the nature of this polymorphism is still unknown (G. Utermann et al., 1982, J. Biol. Chem. 257: 501–507). Rather little is known, either, about the physiological role of apoAIV. It is known that it can activate lecithin-cholesterol acyltransferase (LCAT) in vitro (Steinmetz et al., 1985, J. Biol. Chem., 260: 2258–2264) and that it is able, like apolipoprotein AI, to interfere with the attachment of the HDL particles to bovine aortic endothelial cells (Savion et al., 1987, Eur. J. Biochem., 257: 4171–4178). These two activities indicate that apoAIV very probably intervenes as a mediator of the reverse transport of cholesterol. The gene for apoAIV has been cloned and described in the prior art (see, in particular, WO 92/05253 and Elshourbagy et al., J. Biol. Chem., 1987, 262(17), 7973–7981). Those proteinaceous products having an activity of the apolipoprotein AIV type which may be mentioned are, in particular, the fragments and derivatives described in patent application FR 92 00806.

Apolipoprotein E comprises 317 residues, 18 of which correspond to the signal peptide. There is no propeptide. The gene for apoE has been cloned and sequenced (approximately 3600 bp) and encodes an mRNA of 1163 bp (Das et al., J. Biol. Chem., 1985, 260, 6240–6247). In the plasma, apoE is distributed between the VLDL and the HDL particles. It represents approximately 10–20% of the VLDL proteins and 2% of the HDL proteins. The HDL-Es constitute a distinct subclass of HDL. The concentration of apoE in the plasma is approximately 0.05 g/l. ApoE is synthesized in the form of a sialoprotein which is then desialylated in the plasma. Synthesis of apoE is carried out by the liver and, to a minor extent, by the intestine. However, in contrast to the other apolipoproteins, apoE is also synthesized in a large number of other tissues (brain, kidney, adrenals, reticuloendothelial cells, etc.). While apoE recognizes the LDL receptor (apoB/E receptor) with very high affinity, it also recognizes another receptor on the hepatic cells which does not recognize apoB (chylomicron/remnant receptor).

A polymorphism has been demonstrated on the basis of differing electrophoretic mobilities. Thus, six major phenotypes (E2/2, E2/3, E2/4, E3/4, E3/3 and E4/4) have been described. According to studies conducted on large caucasian populations, the prevalence of the corresponding alleles is 14–15% for e4, 74–78% for e3 and 8–12% for e2. A difference is found in the case of Finns, for whom e4 is more abundant (23%) and e2 less abundant (4%). The normal allele is e3. The studies indicate that the e2 allele corresponds to type III dyslipoproteinaemia (phenotype E2/2), a disease which is associated with an increase in cholesterol, triglycerides and xanthomas and with premature atherosclerosis. An association between the e4 allele and familial Alzheimer's disease has recently been reported (Strittmatter et al., P.N.A.S. 99 (1993) 1977). More recently, destruction of the gene for apoE in mice has resulted in the appearance of hypersusceptibility to atherosclerosis (E. Rubin et al. Cell 1992).

In general, the inserted genomic DNA sequence also includes sequences which enable it to be expressed in the cell containing it. These sequences can be sequences which are naturally responsible for expressing the said gene when these sequences are able to function in the said cell. They can also be sequences of a different origin (sequences which are responsible for expressing other proteins, or even synthetic sequences). In particular, they can be sequences from eukaryotic or viral genes. By way of example, they can be promoter sequences which are derived from the genome of the cell which it is wished to infect, or from the genome of a virus, in particular the promoters of the adenoviral genes E1A and MLP, the CMV promoter, the RSV LTR promoter, etc. The non-viral promoter sequences which are preferably used are the ApoAI promoters or the hepatic enhancers of ApoE or the intestinal enhancers of apoCIII. Naturally, these expression sequences can additionally be modified by adding activating sequences, regulatory sequences, etc. The genomic DNA can also be included in a large-capacity expression vector such as the P1 vector or else the YAC vectors.

The present invention also relates to protecting a transgenic rabbit, according to the invention, which is capable of interfering in diseases linked to dyslipoproteinaemias.

The invention also relates to a process for obtaining the claimed transgenic rabbit.

More specifically, it relates to a process for obtaining the transgenic rabbit according to the invention by injecting, into a rabbit embryo, at least one exogenous genomic DNA sequence encoding a protein which is capable of interfering in diseases linked to dyslipoproteinaemias, transferring the embryo to a recipient rabbit and, after the birth, checking for the presence of the said genomic DNA sequence in the genome of the neonate rabbit.

The process according to the invention for obtaining the transgenic rabbit is described in more detail in Example 2 below. The implementation of such a process does not present any difficulties to the skilled person who is familiar with the techniques of microinjection, and removal and implantation of embryos.

The present invention also relates to the use of the claimed transgenic rabbit for detecting the activity of therapeutic agents or therapeutic methods with a view to preventing and/or treating diseases linked to dyslipoproteinaemias as well as to the methods for detecting novel compounds using this rabbit and to the compounds which are thus characterized.

The present invention thus affords an animal model which is particularly advantageous for detecting specific therapeutic agents for treating and/or preventing diseases linked to dyslipoproteinaemias, in particular in the field of cardiovascular diseases such as myocardial infarction, angina pectoris, sudden death, cardiac decompensation or cerebrovascular diseases, or in the field of neurological diseases where certain apolipoproteins, such as apoE, appear to play an important role (disorders of neuronal ageing, familial Alzheimer's or neuronal regeneration).

The present invention is described more completely using the examples and figures which follow and which should be considered as being illustrative and not limiting.

EXAMPLE 1

PREPARATION OF THE APO-AI GENOMIC FRAGMENT

A DNA fragment containing the gene encoding human apolipoprotein AI, under the control of its own promoter, was obtained by screening a human genomic library.

To do this, a library of partial EcoRI chromosomal DNA fragments derived from K562 cells was constructed in the bacteriophage Charon 4a. This library was then screened by hybridization with a DNA probe which was complementary to human apolipoprotein AI.

Figure 1:
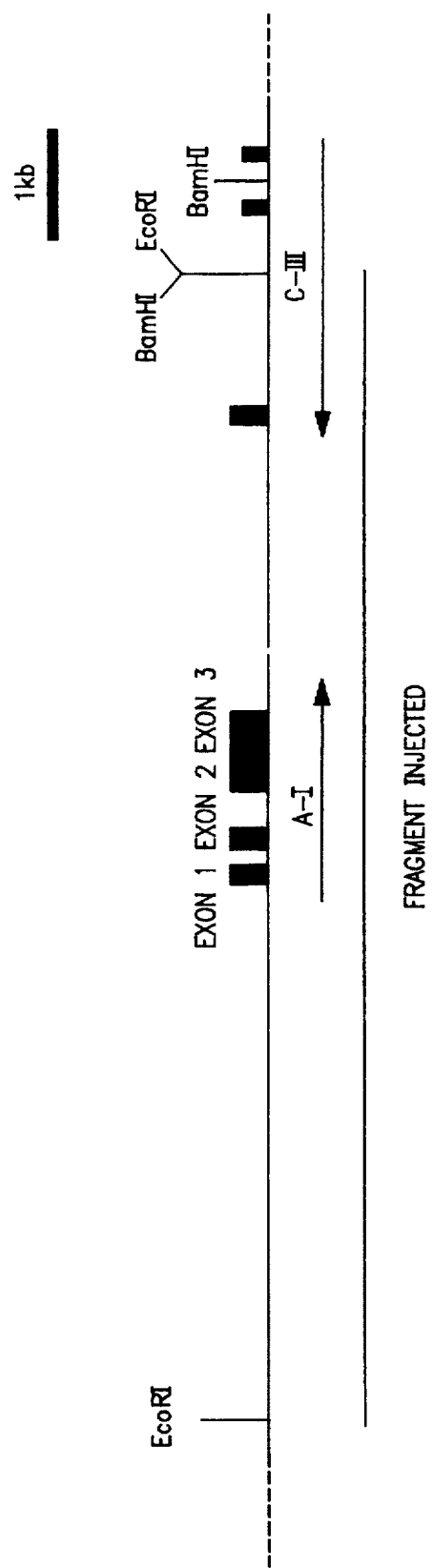
FIG. 1: Depiction of the genomic DNA encoding apolipoprotein AI.

The clone K 3-5-10 was isolated in this screening and analysed by comparison with the published restriction maps for the AI/CII/AIV genomic complex (S. K. Karathanasis et al., Proc. Natl. Acad. Sci. USA, 80, 6147–6151, 1983. S. K. Karanthanasis, Proc. Natl. Acad. Sci. USA, 82, 6374–6378, 1985). It contains, in particular, an EcoRI fragment of approximately 12.5 kbases which hybridizes with the DNA which is complementary to Apo-AI (cf. FIG. 1).

Phage K3-5-10 was amplified in solid medium and its DNA was prepared using standard techniques. The EcoRI/BamHI restriction fragment (digestion with BamHI enables this fragment to separate well on an agarose gel) containing the gene for ApoAI was then purified using a preparative agarose gel and dialysed against a solution of 10 mM tris, pH 7.5, 0.1 nM EDTA prior to injection.

EXAMPLE 2

GENERATION OF TRANSGENIC RABBITS ACCORDING TO THE INVENTION

Superovulation of 28 5-month old female New Zealand rabbits was induced by injecting 0.375 mg of porcine FSH (follicle-stimulating hormone) in the morning and in the evening of 1 day, then 0.782 mg of porcine FSH in the morning and in the evening of the following day and finally 0.375 mg of porcine FSH in the morning of the 3rd day. At about 4 p.m. on the same day, the 16 female rabbits, in a state of superovulation, were put together with males of the same breed in order to be fertilized. At the conclusion of the fertilization, 0.33 mg of LH (luteinizing hormone) are injected into each female rabbit. On the morning of the 4th day, the females were separated from the males and then sacrificed. The embryos are removed by washing the uterus of each female rabbit.

The eggs, still agglutinated by a follicular tissue, are soaked for approximately 20 minutes in a solution of hyaluronidase. They are then washed twice in Brinster's solution. In order to manipulate them subsequently under the microscope, the eggs were deposited in a drop of Brinster-HEPES solution which was supplemented with cytochalasin. This solution increases the resistance of the egg to the injection.

The eggs were selected by observing them under the microscope (100× and 200× magnification) and cultured in B2 Menezo medium. Approximately 500 embryos were kept for the microinjection.

On this same fourth day, within a very short period of the order of 30 minutes after their removal, the embryos are given, by microinjection into the male pronucleus, 2 picolitres of a solution of the DNA, which is obtained in accordance with Example 1. The DNA is at a concentration of 2.5 pg/ml in 10 mM tris, pH 7.5, 0.1 mM EDTA.

These microinjected embryos were then shared out between 24 female New Zealand rabbits in a state of pseudopregnancy. Of these 24 rabbits, only 3 did not take their pregnancy to term. 41 baby rabbits were born, together with 3 which were stillborn.

In order to identify the transgenic animals, the 41 baby rabbits were analysed in the following manner: the DNA which is extracted from a portion of the tail which is removed from each baby rabbit is analysed by PCR for the presence of the human genomic DNA encoding ApoAI. The following primers 5'-TGGCTTTCTCGCCAAGTGTCTTCAGGTGG-3' (SEQ ID NO:1) and 5'-GACAGCGGCAGAGACTATGTGTCCCAGTTTGAA-3' (SEQ ID NO:2) are specific for the human ApoAI sequence and enable a fragment of 800 bp to be amplified in the transgenic animals.

6 transgenic baby rabbits, out of the 41 which were analysed, were identified in this manner.

It was subsequently verified that the transgenic rabbits transmitted the Apo-AI gene to their progeny.

EXAMPLE 3

CHECKING FOR THE EXPRESSION OF HUMAN APOLIPOPROTEIN A-I IN THE PLASMA OF THE TRANSGENIC RABBITS

Fresh blood samples were obtained from the 5-month old transgenic rabbits, and from control rabbits, by removal from the ear after a night of fasting and introduced into tubes containing ethylenediaminetetraacetic acid at a final concentration of 1.5 g/l. After the samples had been withdrawn, these tubes were placed directly into crushed ice. The plasma was obtained by slowly centrifuging at 4° C. for 30 minutes.

The concentration of human apolipoprotein AI was quantified using the APOAIB HYDRAGEL kit (SEBIA, ref. no. 4050), which is an agarose gel kit containing 2 monospecific polyclonal antibodies: anti-apoA-I and anti-apoB. These antibodies are prepared in the rabbit, thereby excluding man/rabbit cross reactivities.

The results of the human apolipoprotein A-I assays which were obtained in the six A-I transgenic rabbits are given in Table I below.

TABLE I

| Rabbit | Human ApoA-I (g/l) |
|---|---|
| No. 1 (male) | 1.00 |
| No. 2 (male) | 1.21 |
| No. 3 (male) | 0.73 |
| No. 4 (male) | 0.17 |
| No. 5 (male) | 0.30 |
| No. 6 (female) | 0.92 |
| Controls (5 males and 5 females | 0.00 |

EXAMPLE 4

MODIFICATIONS OF THE LIPOPROTEIN PROFILES IN THE TRANSGENIC RABBITS

The assays for total cholesterol, triglycerides and HDL (high density lipoproteins) cholesterol were carried out using commercial kits (Boehringer Mannheim, Germany). The different lipoprotein fractions were separated by ultracentrifugation using the method of Havel et al. (R. J. Havel, H. A. Eder and J. H. Bragon, 1955, *J. Clin. Invest.*, vol 34, 1345).

The results of the lipid assays which were obtained in the 6 A-I transgenic rabbits and in the control rabbits, all 5 months of age, are given in Tables II and III.

TABLE II

| Rabbit | Triglycerides (mg/dl) |
|---|---|
| No. 1 (male) | 39.10 |
| No. 2 (male) | 11.80 |
| No. 3 (male) | 15.10 |
| No. 4 (male) | 09.80 |
| No. 5 (male) | 29.40 |
| No. 6 (female*) | 09.50 |
| Controls (5 males and 5 females) | 25.20(8) |

TABLE III

| Rabbit | Cholesterol | | | | VLDL** |
|---|---|---|---|---|---|
| | VLDL mg/dl | LDL mg/dl | HDL mg/dl | Total mg/dl | + LDL-C HDL-C |
| No. 1 (male) | 0.9 | 09.7 | 26.6 | 37.2 | 0.40 |
| No. 2 (male) | 0.4 | 06.0 | 30.9 | 37.3 | 0.20 |
| No. 3 (male) | 1.2 | 11.5 | 19.6 | 32.0 | 0.45 |
| No. 4 (male) | 0.6 | 07.6 | 13.9 | 22.1 | 0.58 |
| No. 5 (male) | 1.2 | 03.1 | 10.8 | 15.1 | 0.39 |
| No. 6 (female*) | 1.5 | 06.6 | 22.5 | 30.6 | 0.36 |
| Controls (5 males & 5 females) | 2.3 (0.5) | 26.1 (5.1) | 23.6 (4.3) | 52.0 (8.2) | 01.20 (0.2) |

*= pregnant female. In brackets = standard deviation
**= very low density lipoprotein.

EXAMPLE 5

PROTECTION OF THE TRANSGENIC RABBITS EXPRESSING APOLIPOPROTEIN A-I AGAINST THE DEVELOPMENT OF ATHEROSCLEROSIS

Figure 2:
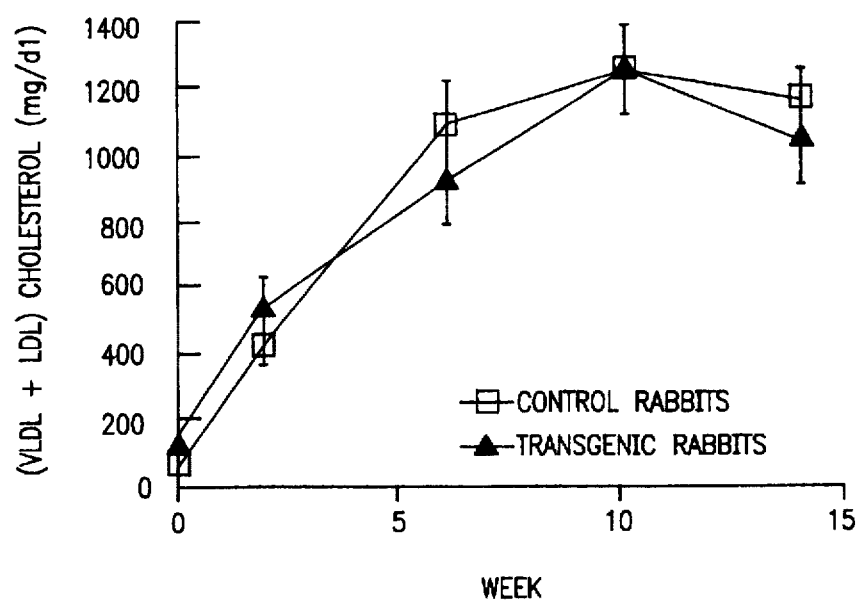
FIG. 2: Concentration of the cholesterol in the VLDL and LDL fractions over the course of a diet which is rich in cholesterol.

In order to evaluate the protection obtained from the apoA-I in the transgenic rabbits derived from line no. 20, we placed these rabbits, and control rabbits, on a cholesterol-rich diet and we adjusted their levels of atherogenic cholesterol, VLDL and LDL cholesterol (FIG. 2). The concentrations of cholesterol increased progressively up to approximately 10–12 g/l between the 6th week of the diet and the end of the diet (14 weeks).

Figure 3:
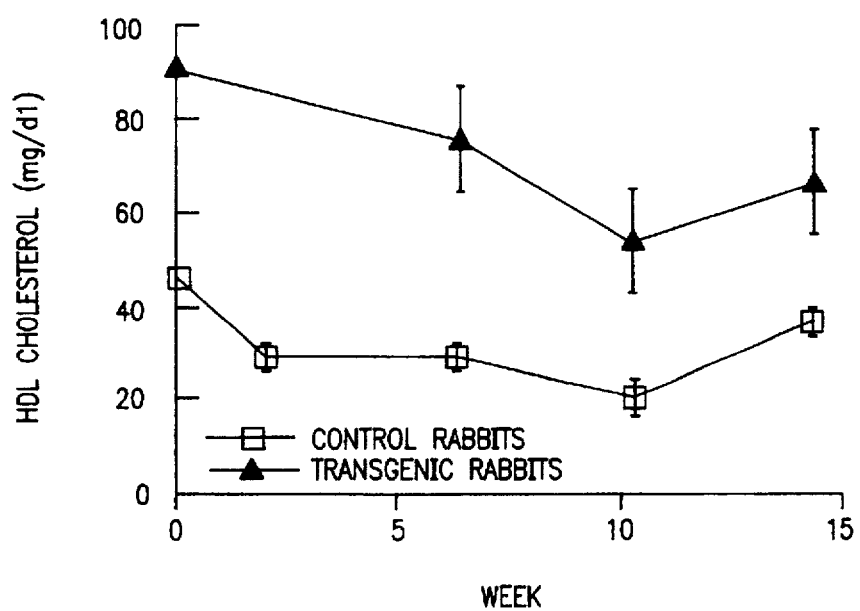
FIG. 3: Concentration in the plasma of the cholesterol in the HDL fraction over the course of a diet which is rich in cholesterol.

The plasma levels of HDL cholesterol were also evaluated. The concentrations of HDL-C were increased approximately 2-fold in the transgenic rabbits as compared with the controls over the whole of the experiment (FIG. 3).

Figure 4:
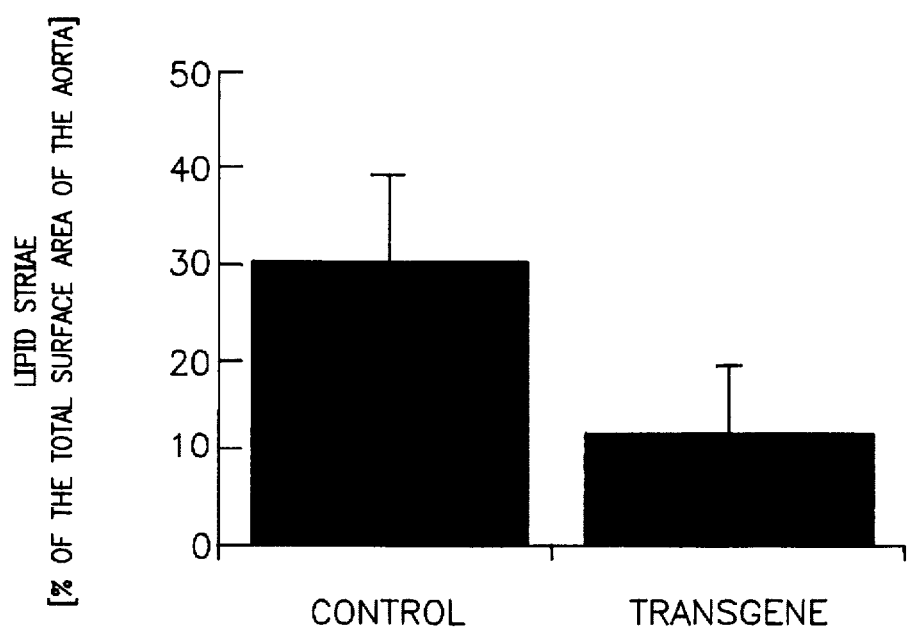
FIG. 4: Evaluation of the damaged surface containing lipid striae in transgenic rabbits and control rabbits.

At the end of the experiment, we assessed the lesions obtained. These lesions are located, in particular, in the aorta, especially in the aortic arch and at the start of the arteries. The use of rabbits in this context enables us to quantify lesions more precisely and to find out about their nature. The results of this experiment demonstrate that the surface area containing the lesions in the transgenic rabbits corresponds to approximately 50% of that observed in the control rabbits (FIG. 4).

Figure 5:
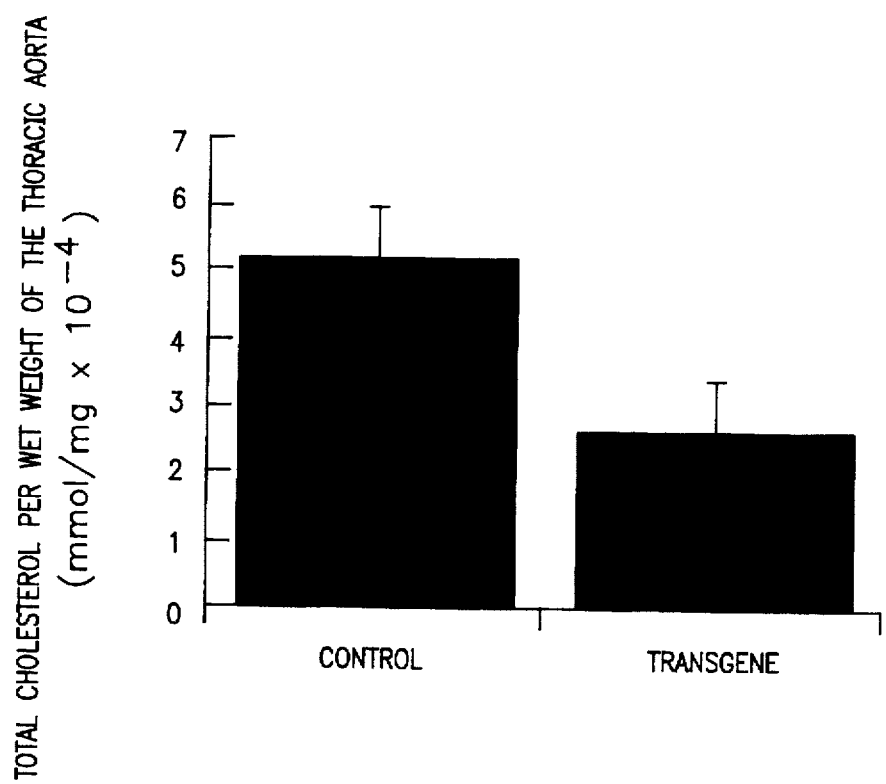
FIG. 5: Comparison of the accumulation of cholesterol in the thoracic aorta of transgenic and control rabbits after a diet of 14 weeks.

The accumulation of cholesterol in the aorta is also significantly lower in the transgenic rabbits than in the controls (FIG. 5).

Figure 6:
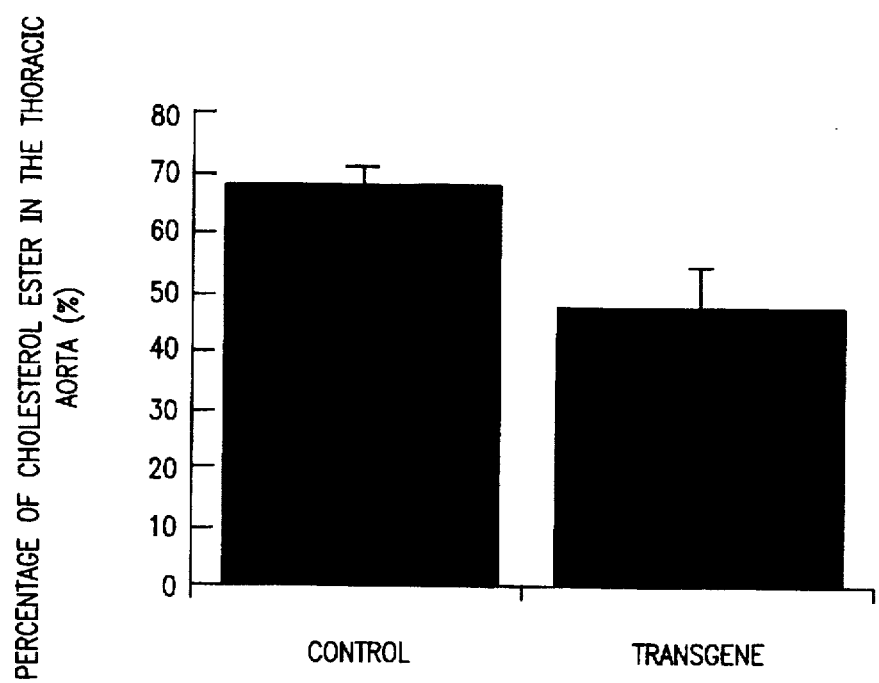
FIG. 6: Comparison of the accumulation of cholesterol esters in the thoracic aorta of transgenic and control rabbits after a diet of 14 weeks.

This difference relates, in particular, to the quantity of cholesterol esters which is found in the aorta. Thus, an accumulation of CEs is observed in the control rabbits which is not found in the transgenic rabbits (FIG. 6).

Therefore, by using the rabbit as a model, we have demonstrated the protective role of apoA-I in the phenomenon of atherosclerosis.

EXAMPLE 6

OBTAINING TRANSGENIC RABBITS WHICH EXPRESS APOLIPOPROTEIN A-I IN A WATANABE GENETIC BACKGROUND

Transgenic rabbit no. 20 was crossed with WHHL (Watanabe heritable hyperlipaemic) females. We detected the presence of the transgene in 8 out of the 15 descendants, all of which were heterozygous for the deficiency in LDL receptor. These 8 rabbits are therefore transgenic for apoA-I and heterozygous for the deficiency in LDL receptors. The concentrations of HDL-C are 70±10 mg/dl in the human apoA-I transgenic rabbits (n=8) as against 35±10 mg/dl in the control rabbits (n=7). The plasma concentration of apoA-I in the transgenic rabbits is 1.00±0.15 mg/dl (n=7).

A male rabbit which was transgenic for human apoA-I and WHHL-heterozygous was then crossed with WHHL females. Half of the rabbits derived from this cross are WHHL-heterozygous while the other half are WHHL-homozygous. These rabbits differ in their plasma levels of total cholesterol, i.e. between 100 and 300 mg/dl for the first group and between 400 and 800 mg/dl for the second group. We obtained 14 rabbits from this cross, several of which possess the human apoA-I transgene, with possession of the transgene being found in both the WHHL heterozygous and WHHL homozygous groups of rabbits.

Thus, by using successive crosses, we have obtained transgenic rabbits which express the human apoA-I in a WHHL homozygous genetic background.

---

We claim:

1. A transgenic rabbit into whose genome is inserted at least one human genomic DNA fragment which encodes apolipoprotein A-I (Apo-AI), wherein plasma levels of the expressed human apoA-I are at least 0.17 mg/ml in said transgenic rabbit, and wherein the expressed human apoA-I protects the rabbit from developing atherosclerotic disorders upon administration of a cholesterol rich diet.

2. The transgenic rabbit according to claim 1 wherein the plasma levels of Apo-AI are 1.0–1.2 mg/ml.

3. The transgenic rabbit according to claim 1, wherein the genomic DNA which encodes Apo-AI is a fragment of about 12.5 kb.

4. The transgenic rabbit according to claim 1, wherein the genomic DNA which encodes Apo-AI is an EcoR1 restriction fragment of human chromosomal DNA that hybridizes with a DNA complementary to Apo-AI.

5. The transgenic rabbit according to claim 1 which is a Watanabe hereditary hyperlipemic (WHHL) rabbit.

6. The transgenic rabbit according to claim 1, wherein the atherosclerotic disorder is accumulation of cholesterol esters.

7. The transgenic rabbit according to claim 1, wherein the atherosclerotic disorder is an aortic lesion.

8. The transgenic rabbit according to claim 1, wherein the atherosclerotic disorder is an accumulation of cholesterol in the aorta.

9. The transgenic rabbit according to claim 1 wherein the protection from the atherosclerotic disorder comprises an increase of HDL cholesterol as compared to a non-transgenic rabbit.

10. The transgenic rabbit according to claim 9, wherein the increase of HDL cholesterol as compared to the non-transgenic rabbit is approsimately 2-fold.

11. A process for obtaining a transgenic rabbit according to claim 1 which comprises injecting into a rabbit embryo at least one human genomic DNA fragment encoding an Apo-I protein, transferring the embryo to a recipient female rabbit, and screening for the presence of said genomic Apo-AI DNA in the genome of the neonate rabbit, assaying for the level of expression of said human Apo-AI DNA, wherein plasma levels of the expressed human ApoA-I are at least 0.17 mg/ml in the transgenic rabbit, and wherein the expressed human ApoA-I protects the rabbit from developing atherosclerotic disorders upon administration of a cholesterol rich diet.

12. The process according to claim 11, wherein the plasma levels of Apo-AI are 1.0–1.2 mg/ml.

13. The process according to claim 11, wherein the genomic DNA which encodes Apo-AI is a fragment of about 12.5 kb.

14. The process according to claim 11, wherein the genomic DNA which encodes Apo-AI is an EcoR1 restriction fragment of human chromosomal DNA that hybridizes with a DNA complementary to Apo-AI.

15. The process according to claim 11, wherein the atherosclerotic disorder is accumulation of cholesterol esters.

16. The process according to claim 11, wherein the atherosclerotic disorder is an aortic lesion.

17. The process according to claim 11, wherein the atherosclerotic disorder is an accumulation of cholesterol in the aorta.

18. The process according to claim 11, wherein the protection from the atherosclerotic disorder comprises an increase of HDL cholesterol as compared to a non-transgenic rabbit.

19. The process according to claim 18, wherein the increase of HDL cholesterol as compared to the non-transgenic rabbit is approsimately 2-fold.

20. A process for detecting compounds which are useful for preventing and/or treating diseases linked to dyslipoproteinaemias, comprising administering a compound to the rabbit according to claim 1, and detecting activity of the compound in preventing or treating dyslipoproteinaemias.

* * * * *